United States Patent
Hedlund

[11] Patent Number: 6,156,022
[45] Date of Patent: *Dec. 5, 2000

[54] ABSORBENT ARTICLE WITH TRANSVERSE BARRIER ELEMENTS

[75] Inventor: Gunilla Hedlund, Ljungskile, Sweden

[73] Assignee: SCA Molnlycke AB, Gothenburg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,636
[22] PCT Filed: Jun. 7, 1995
[86] PCT No.: PCT/SE95/00671
  § 371 Date: Dec. 30, 1996
  § 102(e) Date: Dec. 30, 1996
[87] PCT Pub. No.: WO96/02216
  PCT Pub. Date: Feb. 1, 1996

[30] Foreign Application Priority Data

Jul. 15, 1994 [SE] Sweden .................................. 9402491

[51] Int. Cl.[7] .................................................. A61F 13/15
[52] U.S. Cl. ...................... 604/385.2; 604/385.1
[58] Field of Search .................. 604/385.1–387

[56] References Cited

U.S. PATENT DOCUMENTS 3,848,599 11/1974 Schear .................................. 604/385.1
5,129,893 7/1992 Thoren .................................. 604/385.2
5,554,142 9/1996 Dreier et al. ......................... 604/385.1
5,653,703 8/1997 Roe et al. ............................. 604/385.2

FOREIGN PATENT DOCUMENTS

| 0 355 740 | 2/1990 | European Pat. Off. . | |
| 2573629 | 5/1986 | France | 604/385.1 |
| 9202817 | 1/1994 | Portugal | 604/385.1 |
| WO 92/14429 | 9/1992 | WIPO . | |
| WO 94/143954 | 7/1994 | WIPO . | |

*Primary Examiner*—Mark O. Polutta
*Attorney, Agent, or Firm*—Young & Thompson

[57] ABSTRACT

An absorbent article such as a diaper, an incontinence protector or the like, comprises an elongated absorbent body, enclosed between a proximal liquid permeable cover layer and a distal liquid impermeable cover layer. In order to prevent feces from being transferred to a front, urine absorbing area of the article, there is provided a barrier means which comprises at least two, adjacent to each other, strip-shaped elastic elements extending transversely over the inside of the article. The elements in a flat state of the article are pretensioned in their longitudinal direction and at least in the use state of the article, extend backwards and out from the article, relative to a longitudinal edge of the strip-shaped elements facing towards the article.

8 Claims, 1 Drawing Sheet

ABSORBENT ARTICLE WITH TRANSVERSE BARRIER ELEMENTS

This application is the 35 USC 371 national stage of International application PCT/SE95/00671 filed on Jun. 7, 1995, which designated the United States of America.

The present invention relates to an absorbent article such as a diaper, an incontinence protector or the like, comprising an elongated absorbent body, enclosed between a proximal liquid permeable cover layer and a distal liquid impermeable cover layer, and a barrier means arranged on the proximal cover layer in an area essentially between a front, urine absorbing area and a rear, faeces receving area of the article, to prevent faeces from being transferred to the urine absorbent area.

BACKGROUND OF THE INVENTION

Various means have been previously suggested for preventing transfer of faeces from a rear area of the absorbent article to the front urine absorbing area of the same and to reduce the risk of urine flowing on the inside of the article from the front area thereof to the rear faeces receiving area.

As examples there can be mentioned various forms of transverse barriers arranged on the inside of the article, said barriers protruding up from the inside of the article and thus forming an obstacle for urine or faeces to pass and be directly mixed together on the inside of the article.

For example, WO 92/14429 reveals an absorbent disposable article, where the transverse, bellows-like folds on the inside of the article are made for rapid absorption of urine in pockets between the folds and to form with its outer edges a liquid barrier to prevent urine from flowing along the inside of the article to the rear, faeces receiving area. These bellows-like folds are oriented so that they lie partially overlapping each other in such a manner that, as seen in the direction from the rear portion of the article towards the front portion, the rear bellows-like fold overlaps partially the fold lying immediately in front thereof, etcetera, whereby urine can be caught in the pockets between the overlapping folds and be conducted down into the underlying absorbent body. Such a barrier can, however, not prevent transfer of faeces from the rear portion of the article to its front portion.

SUMMARY OF THE INVENTION

A purpose of the present invention is to achieve an improved barrier, which can effectively brake and stop transfer of faeces from a rear portion of the absorbent article to the front urine absorbing area.

For this purpose, the article described by way of introduction is characterized in that the barrier means comprises at least two strip-shaped, elastic elements lying adjacent to each other and transversely to the article, said strips in a flat state of the article being pretensioned in their longitudinal direction and extending, at least in the use state of the article, backwards and out from the article, relative to a longitudinal side edge of the strip-shaped elements, said edge facing towards the article. By virtue of the fact that the strip shaped elements are elastic and pretensioned in their own longitudinal direction in the flat state of the article and are placed so that their free longitudinal edges extend backwards on the article, the strip shaped elements rise, when the article is worn, obliquely upwards and backwards to form pockets between the elements, the openings of which face towards the rear portion of the article, whereby forward movement of faeces on the inside of the article can be effectively prevented.

Preferably, the strip shaped barrier elements overlap each other partially, at least on the flat state of the article.

The strip shaped elements themselves can be made in a number of manners within the scope of the invention. According to a preferred embodiment, the strip shaped elements have the shape of bellows folds in the inner proximal cover layer. Alternatively, the strip shaped elements can have the form of bellows folds in a surface layer applied on top of the proximal cover layer. The strip shaped elements can also consist of separate strips applied on the proximal cover layer.

The strip shaped barrier elements are suitably fixed to the article at its lateral edges, for example by glueing in a flat state of the elements.

The elastic characteristic of the strip shaped elements can be achieved, for example, by laying an elastic element in the outer free longitudinal edge of each strip shaped element, whereby the strip when formed or applied to the article in a flat state is imparted a certain amount of pretensioning, which when the article is worn strives to lift up the strips somewhat from the inner surface material to a rearwardly inclined position to form a plurality of parallel pockets between the strip shaped elements, said pockets forming an effective braking barrier for faeces in the direction towards the front urine absorbing portion of the article.

It is suitable that the strip shaped elements each extend transversely over the article beginning from a narrow crotch area of the same and towards the front wet area of the article.

BRIEF DESCRIPTION OF THE DRAWINGS

The invention will be described in more detail below with reference to the accompanying drawing, where.

DETAILED DESCRIPTION OF THE INVENTION

Figure 1:
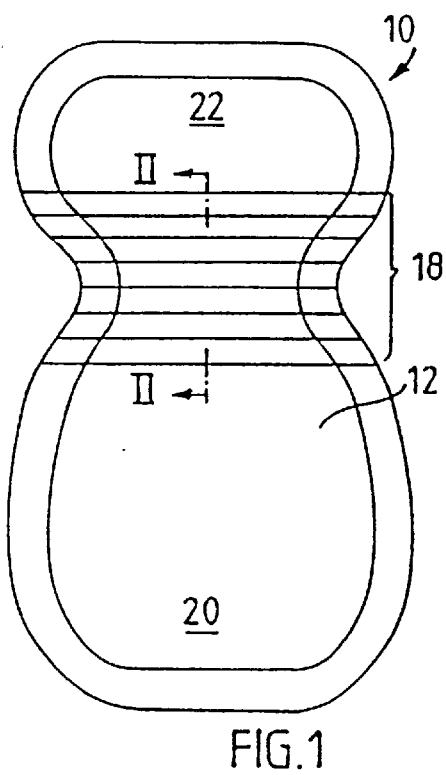
FIG. 1 is a plan view of a diaper provided with barrier elements in accordance with the present invention.

In FIG. 1, an absorbent article 10 is shown in the form of a diaper or an incontinence protector, comprising an elongated, essentially hour-glass shaped absorbent body, 12, which in a manner known per se is enclosed between a liquid permeable inner surface layer 14 located closest to the wearer, and a liquid impermeable outer layer 16 of, for example, polyethylene or polypropolyne, which surface layers 14, 16 are joined to each other along the peripheral edge of the article 10. The absorbent body 12 consists of liquid absorbing material which is known per se of a type suitable to the purpose, for example fluff pulp, possibly incorporating superabsorbent polymer material, which means material capable of absorbing liquid many times its own weight.

The inner surface layer 14 can be made of a plastic material which is of itself liquid impermeable, but which is made liquid permeable by perforation thereof, or a material which is liquid permeable in itself, such as non-woven material, for example fibre cloth.

In accordance with the invention, there is formed on or in the inner cover layer 14, a barrier means, generally designated 18, the function of which is to prevent or in any case strongly impede faeces received in the rear portion 20 of the article from being transferred or spread in a direction forwards to the forward urine absorbing area 22 of the article 10.

Figure 2A:
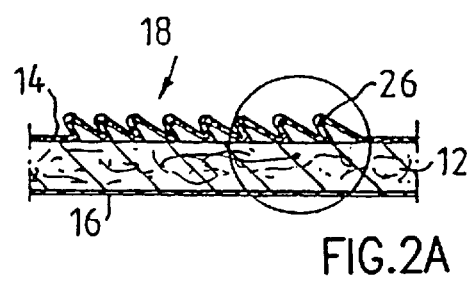
FIG. 2A is a longitudinal section taken along the line 2—2 in FIG. 1.
Figure 2:
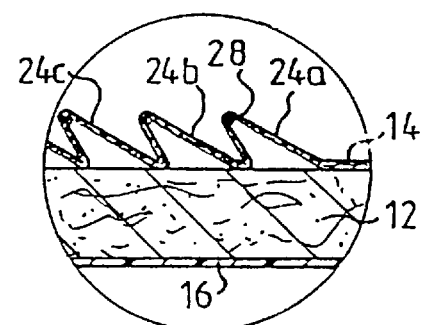
FIG. 2 is a detailed depiction of the encircled portion in FIG. 2A.

As can be seen in more detail in FIG. 2A and FIG. 2, the barrier means 18, in accordance with a first embodiment of the invention, can be formed of a plurality of successive, transverse fold formations 24a, 24b, 24c . . . etc., formed in the inner cover layer 14 itself, said fold formations 24a . . . forming double-walled, strip-like elements, which in the flat state of the article partially overlap each other in such a manner that, as seen in the direction from the forward portion of the article towards its rear portion, the forward strip-like fold formation 24a partially overlaps the subsequent fold formation 24b, which in turn partially overlaps the subsequent fold formation 24c, etc. Thus, the strip-shaped fold formations 24a . . . extend backwards and outwards from the article 10 relative to a longitudinal edge, facing towards the article, of the strip-shaped barrier elements, i.e. they lie directed obliquely backwards in a fish-scale or sawtooth pattern. In order to ensure, when using the article, that the outer longitudinal edge 26 of each strip-shaped barrier element 24a . . . is raised some-what above the adjacent underlying strip-shaped element, a pretensioned elastic element 28 is disposed along the outer longitudinal edge 26 of each strip element 24a . . . , thereby creating open, parallel pockets between the strip-shaped elements 24a . . . , which prevent faeces from being spread forward to the front, urine absorbing area of the article 10 and there coming into contact with the genitals of the wearer. The pretensioning in the elastic elements 28 should be selected to be great enough that the strip-shaped barrier elements 24a . . . are caused to be lifted somewhat during use. The elastic elements can, for example, consist of elastic bands, threads, films, fibre cloth or the like.

The strip-shaped barrier elements 24a . . . are flattened and are fixed to each other, for example by means of glueing, at their end portions, suitably in the area of the lateral edges of the absorbent article 10, where the upper and lower cover layers 14, 16 are fixed to each other. The folded barrier strips 24a . . . are primarily located in the crotch area of the article, but can also be placed slightly into the front area of the article.

Within the scope of the invention, it is possible to make the barrier means 18, consisting of parallel strip-like elements, in a number of different manners. As is shown in FIG. 3, the article 10 can have two surface materials 14a, 15 on the inside, one external layer 14a being folded in the same manner as the layer 14 in FIG. 2 and being placed on top of a second liquid permeable layer 15 disposed previously or at the same time.

According to an additional embodiment of the barrier means according to the invention (FIG. 4), it can be formed of a plurality of separate, parallel strips 30 of fibre cloth, for example, which has been glued to the inside of a previously manufactured absorbent article in a somewhat overlapping relationship to each other.

Figure 3:
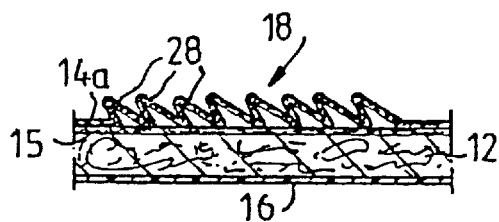
FIG. 3 shows a similar longitudinal section as in FIG. 2 but with an alternative embodiment of the barrier elements according to the invention.
Figure 4:
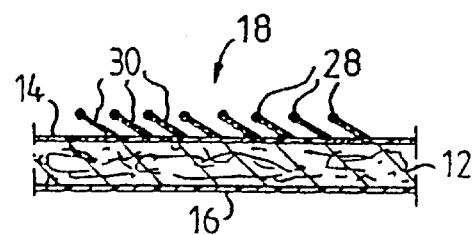
FIG. 4 shows a further embodiment of the barrier elements according to the invention in longitudinal section.

The embodiment according to FIGS. 3 and 4 are both provided with elastic elements 28 in a manner similar to the embodiment according to FIG. 2. Other methods of fixing the end portions of the strip-shaded barrier elements to each other are conceivable, for example ultrasonic welding. In those cases where the barrier means are formed of separate strips, these can of course be ultrasonically welded instead of being glued.

What is claimed is:

1. An absorbent article extending in a longitudinal direction, and comprising an elongated absorbent body, enclosed between a proximal liquid permeable cover layer and a distal liquid impermeable cover layer, and a barrier means arranged on the proximal cover layer in an area essentially between a front, urine absorbing area and a rear, feces receiving area of the article, to prevent feces from being transferred to the urine absorbing area, wherein the barrier means comprise a plurality of strip-shaped elastic elements lying adjacent to each other and transversely to the longitudinal direction of the article, said strip-shaped elements partially overlapping each other in a flat state of the article being pretensioned in their longitudinal direction, and extending, at least in a use state of the article, rearwardly and out from the article, relative to said front urine absorbing area.

2. The article according to claim 1, wherein the strip-shaped elements have the shape of bellows or accordion folds in the proximal cover layer.

3. The article according to claim 1, wherein the strip-shaped elements have the shape of bellows or accordion folds in a surface layer disposed on top of the proximal cover layer.

4. The article according to claim 1, wherein the strip-shaped elements consist of separate strips disposed on the proximal cover layer.

5. The article according to claim 1, wherein the strip-shaped elements are fixed to the article at their lateral limiting edges.

6. The article according to claim 1, further comprising an elastic element which is disposed along a free longitudinal edge, facing away from the article, of the strip-shaped element.

7. The article according to claim 1, wherein the plurality of adjacent strip-shaped elements which form a series of parallel pockets between the strip elements.

8. The article according to claim 7, wherein each of the strip-shaped elements extends transversely over the article beginning from a narrow crotch area of the article and towards the front urine absorbing area.

* * * * *